United States Patent [19]

Lin et al.

[11] 4,079,138
[45] Mar. 14, 1978

[54] PERMANENT SUSPENSION PHARMACEUTICAL DOSAGE FORMS

[75] Inventors: Song-Ling Lin; Maturu K. Pramoda, both of Rouses Point, N.Y.

[73] Assignee: American Home Products Corporation, New York, N.Y.

[21] Appl. No.: 726,383

[22] Filed: Sep. 24, 1976

Related U.S. Application Data

[62] Division of Ser. No. 537,867, Jan. 2, 1975, Pat. No. 3,996,355.

[51] Int. Cl.² ............................................. A61K 31/54
[52] U.S. Cl. .................................................. 424/246
[58] Field of Search ......................................... 424/246

[56] References Cited

U.S. PATENT DOCUMENTS

| | | | |
|---|---|---|---|
| 4,029,655 | 6/1977 | Cise | 424/246 |
| 4,036,833 | 7/1977 | Ishimaru et al. | 424/246 |

*Primary Examiner*—Dale R. Ore
*Attorney, Agent, or Firm*—Stephen Venetianer

[57] ABSTRACT

Permanent suspension dosage forms of drugs, particularly of the water-sensitive type, for administration without reconstitution are disclosed. The suspensions contain a drug dispersed in an anhydrous vegetable oil vehicle containing a saccharide as the suspending agent. These suspensions in dosage unit form exhibit long term stabilities, extended shelf lives, and excellent taste characteristics.

4 Claims, No Drawings

PERMANENT SUSPENSION PHARMACEUTICAL DOSAGE FORMS

This is a division, of application Ser. No. 537,867 filed Jan. 2, 1975 now U.S. Pat. No. 3,996,355.

BACKGROUND OF THE INVENTION (a) Field of the Invention

This invention relates to permanent suspension dosage forms of water sensitive drugs particularly suitable for oral administration without reconstitution. These dosage forms have exhibited unique long term stabilities and extended shelf lives. They possess excellent taste characteristics, and bioavailabilities.

(b) Prior Art

Commercial aqueous suspension of antibiotics for oral administration have limited shelf lives because of the instability of the antibiotic in aqueous media. For example, commercial ampicillin oral suspensions, after reconstitution with water according to manufacter's instructions will decompose about 0.2% per day at 4° C. and 0.6% per day at 25° C. Therefore, these dosage forms must be marketed dry, as a powder, for reconstitution with water immediately prior to dispensing to the patient.

U.S. Pat. No. 3,097,135 describes a prior art approach to overcoming this instability problem by providing a method for the stabilization of erythromycin in an anhydrous emulsion for oral administration. A variety of emulsifying agents and processing temperatures of 85°–90° C are described.

West German Offenlegungsschrift No. 2,250,680 describes the preparation of stable suspensions suitable for antibiotics which employ a variety of "necessary agents", including an emulsifying agent, "in the proper ratio" to achieve a suspension alleged to be stable, although without any supporting data.

Oral pharmaceutical compositions employing mono-, di-or triglycerides of saturated acids having 6 to 12 carbon atoms as "adsorption promoting agents" for a variety of drugs are described in Belgian Pat. No. 807,312. The thrust of this patent is to facilitate the gastro-intestinal adsorption of the drug, thus, intensifying or promoting its therapeutic effect. No stability data or shelf-life characteristics of the resulting compositions are given.

It is an object of this invention to provide permanent suspensions of drugs dispersed in an anhydrous vehicle constituting a unique structurized suspension. The compositions of this invention do not require heat during manufacture, nor do they require emulsifying agents to achieve commercially acceptable stability and exceptional shelf-life.

SUMMARY OF THE INVENTION

It has been found that stable suspensions suitable for oral administration are provided by suspending a therapeutically effective amount of a water sensitive drug in an anhydrous vehicle comprising a sugar and a vegetable oil, said sugar suitable, and present in an amount sufficient, to cause a suspension to form. Also constituting a novel embodiment of this invention is the foregoing anhydrous vehicle.

A preferred embodiment of this invention is a vegetable oil vehicle with a suitable pharmaceutically acceptable thickening agent, effective to thicken the oil, and a sugar. The water sensitive drug is dispersed in the resulting structurized suspension. No heating is required to prepare a stable suspension. Good stability of the water sensitive drug in such permanent suspension form results. Bioavailability equal to that of the commercially available aqueous suspensions has been demonstrated.

Exemplary of such a preferred embodiment is a therapeutically effective amount of a drug, selected from the group consisting of aspirin, amoxicillin, ampicillin, amoxicillin in combination with probenecid, and ampicillin in combination with probenecid suspended in an anhydrous vegetable oil vehicle comprising from about 5 to about 60% sucrose and from about 0.1 to about 5% silica thickening agent. The foregoing percentages are by weight of total suspension which in unit dosage form contains conventional pharmaceutically acceptable excipients selected from preservatives, antioxidants, flavors and colors. Before bringing a batch unit dosage suspension to final volume or weight, conventional concentrations of selected pharmaceutical excipients can be introduced.

DETAILS OF THE INVENTION

Typically an oral unit dosage form of the permanent suspensions of the invention contains the drug, (generally of the water-sensitive type), thickening agent, sugar, i.e., saccharide, vegetable oil, preservative, antioxidant, flavoring, and color. Each of these ingredients is discussed in more detail hereinafter.

Although any drug which is stable in the presence of a vegetable oil vehicle can be employed as the pharmaceutically active component in the novel suspensions of this invention, particular noteworthy advantages are manifested in the cases of formulations incorporating water-sensitive drugs, and specifically those water-sensitive drugs having a bitter taste. Antibiotics, Clofibrate aspirin and disulfiram are exemplary of drugs which can advantageously be employed. Illustrative of the antibiotics are those of the penicillin family, such as the penicillins (eg. penicillin V, penicillin G, penicillin K), ampicillin, amoxicillin, oxacillin, cloxacillin, flucloxacillin, dicloxacillin, phenethicillin, propicillin, carbenicillin, methicillin and other synthetic or semi-synthetic penicillins; the tetracycline family, such as tetracycline, chlortetracycline, or oxytetracycline; other antibiotics, such as kitasamycin, erythromycin, the cephalosporins, griseofulvin, rapamycin, chloramphenicol; or antibiotics in combination with one or more drugs, including the foregoing representative antibiotics. Representative of such combinations are amoxicillin or ampicillin in combination with probenecid, or with aspirin.

For convenience and to avoid undue prolix, the drugs set forth herein are described by the appropriate generic name. As used herein, however, the generic name includes (in those cases where they exist) the free acid or base (ie. amphoteric) form, the anionic salts with acids, such as inorganic acids (eg. hydrochloric acid, sulfuric acid, etc.), the cationic salts with bases such as sodium hydroxide, potassium hydroxide, procaine, or benzathine, amides and esters such as the tartrate. Also included are the anhydrous and hydrated forms where applicable, eg. ampiclillin.

Although various sugars can be employed as a component of the novel permanent suspensions of the invention, sucrose is highly preferred. Extraopolated room temperature stability studies of a sucrose-sesame oil-ampicillin system revealed an extraopolated shelf-life (30° C) for this system to be greater than five years. When mannitol (chosen for its comparable taste masking characteristics) was substituted for sucrose in the same system the extrapolated shelf-life was not more than one year. Exemplary of the other saccharides (ie. mono-, di-, or poly-) which can be employed are lactose, fructose, glucose, mannitol, or sorbitol.

The sugar can be employed in any pharmaceutically acceptable form. For example, in the case of sucrose, it can be employed as sucrose, U.S.P.; pulverized sucrose or confectionary sucrose.

The vegetable oil vehicle can be any natural or synthetic pharmaceutically acceptable vegetable oil, such as peanut oil, soy bean oil, corn oil, sesame oil, cottonseed oil, acetylated glycerides, ethyl oleate, mineral oil, mono- or di- fatty acid esters of polyethylene glycols, or glyceryl mono-oleate. The oils comprise a mono-, di-, or triglyceride, alone or in combination, prepared from saturated fatty acids. It is preferred that the oil be a glyceryl ester of a $C_{14}$–$C_{22}$ saturated and/or unsaturated fatty acids. Preferred vegetable oil vehicles are, peanut oil, coconut oil, corn oil, and sesame oil which is especially preferred. Fatty acids having from about 6 to about 20 carbon atoms can be employed.

Although the drugs incorporated in the permanent suspensions of this invention exhibit excellent stability, with shelf lives exceeding five years in some cases, (as, for example, with ampicillin), it has been found that an exceptionally elegant suspension can be obtained by the incorporation of a silica agent. These suspensions exhibit excellent shelf lives, with minimal percent oil separation, and provide pseudoplastic viscosity of the permanent suspension.

Various grades of silica available commercially can be employed. Exemplary are those available under the SYLOID brand name from W. R. Grace & Co., Davison Chemical Division, Baltimore, Md. 21203; the CAB-O-SIL brand name from Cabot Corporation, Boston, Mass.; or the aerosil name from Dow-Corning Corp., Midland, Mich. or Degussa, Frankfort, W. Germany.

It has been found that silica agents exhibiting certain parameters impart exceptional characteristics to the novel suspensions of this invention. The preferred characteristics of the silica agent are an "oleophilicity" of about one, a slightly alkaline pH in water, and a particle size range of 2 to 4 microns. ("oleophilicity" is defined as the ratio between oil absorption lbs./100 lbs. and the surface area $M^2$/gm., of the silica gelling agent). Maximum and effective thickening and minimum oil separation upon aging occurs with those silicas having an oleophilicity of about one. Expecially preferred silica agents are those exemplified by SYLOID grades 266-86 and 244-68 (as defined in Davison Product brochure PA 59-371 entitled "Family of SYLOID Silicas at Work") including the following physical-chemical properties: An alkaline pH (5% aqueous slurry) of no higher than eight, preferably about 7.6; an oleophilicity (as herein defined) of 0.75 to 1.4 and preferably 0.90–1.10, and a particle size density (gms./ml.) of about 0.55.

In preparing the stable suspensions of this invention in pharmaceutical unit dosage form, minor amounts of conventional and commercially available pharmaceutical excipients (ie, acceptable, pharmaceutical grade preservatives, antioxidants, flavors and colors) can be employed, provided each is compatible with the drug-vehicle system involved. Exemplary of such excipients are preservatives selected from the parabens (eg. propylparaben), benzyl alcohol or phenol; antioxidants selected from ascorbyl palmitate, butylated hydroxytoluene, butylated hydroxyanisole or tertiary butyl hydroquinone; flavors selected from imitation banana or chocolate (eg. 59.256/A or 57.328/A respectively, Firmenich, Inc., N.Y.), imitation orange (eg. V. 30795 International Flavors and Fragrances, N.Y.).

The range of ingredients in the permanant suspension formulation of this invention can vary from about 5 to about 60 percent of the sugar, from about 0.1 to about 5.0 percent of the silica agent, a pharmaceutically effective amount of the selected drug, conventional minor amounts (eg. less than about 5%) of pharmaceutical excipients, and the vegetable oil vehicle which constitutes the balance of the total suspension. The preferred amounts of sugar and silica agent range from about 20 to about 40% and about 0.5 to about 1.5% respectively. (As used herein, all percentages are by weight based on total suspension unless otherwise stated.)

The preparation of the novel suspensions herein described is simple and straight-forward. In general it involves the following sequences:

A. Add the sugar, in successive portions, to a portion of vegetable oil in a suitable blender and stir to suitably disperse and suspend the system.

B. Add silica (eg. SYLOID or CAB-O-SIL) agent and stir until dispersed.

C. Add drug and stir until a suspension is obtained

D. Optimally add pharmaceutical excipients (eg. preservative, flavor, dye, antioxidant) and stir for a few minutes. (Optional)

E. Add sufficient additional vegetable oil to bring the final weight of the batch to 100 parts by weight and stir to obtain a uniform suspension.

The absence of a heating step is a unique feature of the process of this invention. The process is also unique in not requiring an emulsifying or antiprecipitation agent to achieve stable suspensions with minimal oil separation. Furthermore, the process does not require the use of special mixing equipment capable of a high degree of pulverization at critical temperatures. (Compare West German Offenlegungsschrift No. 2,250,680 of May 10, 1973, and Belgian Pat. No. 807,312, filed Nov. 14, 1973. )

The following examples demonstrate this invention:

EXAMPLES

1. Amoxicillin Permanent Suspension
   A. Formula for 25 mg/ml

| | | |
|---|---|---|
| Amoxicillin Trihydrate | 2.50 | Gm. |
| Sucrose, Powdered | 20.00 | Gm. |
| CABOSIL | 1.25 | Gm. |
| Sesame Oil q.s. | 100.00 | ml. |

Stability Data

| Storage Conditions | Amoxicillin Recovered |
|---|---|
| Initial | 24.4 mg/ml |
| 3 days at 80° C | 23.2 |
| 7 days at 80° C | 22.7 |
| 10 days at 80° C | 21.6 |
| 14 days at 80° C | 19.2 |
| 30 days at 80° C | 14.6 |
| 3 days at 74° C | 23.5 |
| 14 days at 74° C | 21.7 |
| 7 days at 62° C | 23.4 |
| 2 months at 62° C | 22.3 |
| 2 months at 51° C | 23.9 |
| 3 months at 51° C | 22.1 |
| 12 months at 40° C | 22.7 |
| 12 months at 30° C | 23.3 |

Based on these data, it is estimated that the formula will be stable for at least 3 years at room temperature.

B. Formula for 50 mg/Gm. (made in research laboratory)

| | | |
|---|---|---|
| Amoxicillin Trihydrate | 5.00 | Gm. |
| Sucrose, Powdered | 27.50 | Gm. |
| SYLOID (266-86) | 1.00 | Gm. |
| Citric Acid | 0.01 | Gm. |
| Propyparaben | 0.10 | Gm. |
| Tert. Butylhydroquinone | 0.02 | Gm. |
| Imitation Chocolate | 0.20 | Gm. |
| Cocoa | 1.00 | Gm. |
| Sesame Oil, q.s. | 100.00 | Gm. |

Stability Data

| Storage Conditions | Amoxicillin Recovered |
|---|---|
| Initial | 51.1 mg/Gm. |
| 3 days at 80° C | 46.5 |
| 1 week at 80° C | 36.5 |
| 2 weeks at 80° C | 15.8 |
| 1 week at 74° C | 45.4 |
| 2 weeks at 74° C | 38.7 |
| 1 month at 74° C | 20.8 |
| 2 months at 74° C | 14.0 |
| 1 month at 62° C | 46.2 |
| 2 months at 62° C | 43.5 |
| 4 months at 62° C | 34.2 |
| 6 months at 30° C | 51.8 |

Based on these data, it is estimated that the formula will be stable for at least 3 years at room temperature.

In a crossover 24-subject bioavilability study, Amoxicillin Permanent Suspension as described above was compared with a commercial Amoxicillin Aqueous Suspension* (reconstituted with water according to the label instruction of the manufacturer prior to oral administration). Amoxicillin serum concentrations expressed in mcg/ml after oral dose of 5 ml. suspension are shown below:

| Time in Hours After Oral Administration | Drug Concentration in Serum, mcg/ml | |
|---|---|---|
| | Permanent Suspension | Aqueous Suspension |
| 0 | 0.00 | 0.00 |
| 0.5 | 3.00 | 4.89 |
| 1 | 5.45 | 6.26 |
| 1.5 | 5.08 | 4.69 |
| 2 | 3.86 | 3.34 |
| 3 | 1.82 | 1.69 |
| 4 | 0.83 | 0.77 |
| 5 | 0.37 | 0.33 |
| 6 | 0.15 | 0.13 |
| 8 | 0.02 | 0.00 |

*Amoxil Suspension, Ayerest, McKenna and Harrison, Ltd. Montreal, Canada

The equivalency between these two dosage forms (i.e. Amoxil and 1.C.) is clearly demonstrated.

C. Formula for 50 mg/Gm. (made in production facility)

| | | |
|---|---|---|
| Amoxicillin Trihydrate | 5.00 | Gm. |
| Sucrose, Powdered | 27.50 | Gm. |
| SYLOID (266-86) | 1.00 | Gm. |
| Citric Acid | 0.01 | Gm. |
| Propylparaben | 0.10 | Gm. |
| Tert. Butylhydroquinone | 0.02 | Gm. |
| Imitation Chocolate | 0.20 | Gm. |
| Cocoa | 1.00 | Gm. |
| Sesame Oil, q.s. | 100.00 | Gm. |

Stability Data

| Storage Conditions | Amoxicillin Recovered |
|---|---|
| Initial | 47.0 mg/ml |
| 1 day at 80° C | 43.9 |
| 3 days at 80° C | 40.5 |
| 5 days at 74° C | 45.1 |
| 2 weeks at 62° C | 44.4 |
| 1 month at 62° C | 45.9 |
| 2 months at 51° C | 46.4 |

Based on these data, it is estimated that the formula will be stable for about 3 years at room temperature.

D. Tert. Butylhydroquinone can be eliminated from Formulation B without significantly altering the chemical stability of the product.

E. Propylgallate can be used to substitute tert. butylhydroquinone in Formulation B without significantly altering the physical and chemical stability of the product.

F. Polysaccharides, disaccharides and monosaccharides, such as sorbitol, mannitol, lactose, glucose or fructose can be substituted for sucrose in Formulation B.

2. Ampicillin Permanent Suspension

A. Formula for 50 mg/Gm. of Ampicillin

| | | |
|---|---|---|
| Ampicillin Trihydrate | 5.00 | Gm. |
| Sucrose, Powdered | 35.00 | Gm. |
| SYLOID (266-86) | 0.75 | Gm. |
| Imitation Chocolate | 0.15 | Gm. |
| Cocoa | 1.00 | Gm. |
| Sesame Oil, q.s. | 100.00 | Gm. |

Stability Data

| Storage Conditions | Ampicillin Recovered |
|---|---|
| Initial | 48.4 mg/Gm. |
| 8 hr. at 80° C | 42.1 |
| 16 hr. at 80° C | 35.4 |
| 1 day at 80° C | 26.7 |
| 1 day at 74° C | 41.3 |
| 2 days at 74° C | 33.7 |
| 3 days at 74° C | 22.1 |
| 1 wk. at 62° C | 53.8 |
| 2 weeks at 62° C | 52.5 |
| 3 weeks at 62° C | 47.9 |
| 3 weeks at 30° C | 49.1 |
| 7 months at 30° C | 51.7 |

Based on these data, it is estimated that the formula will be stable for at least 3 years at room temperature.

B. Formula for 100 mg/Gm.

| | | |
|---|---|---|
| Ampicillin Trihydrate | 10.0 | Gm. |
| Sucrose, Powdered | 40.0 | Gm. |
| CABOSIL | 1.0 | Gm. |
| Corn Oil, q.s. | 100.0 | Gm. |

Stability Data

| Storage Condition | Ampicillin Recovered |
|---|---|
| Initial | 90.2 |
| 1 day at 80° C | 33.0 |
| 2 weeks at 62° C | 75.7 |
| 18 days at 51° C | 88.7 |
| 8 weeks at 51° C | 80.9 |
| 13 months at 40° C | 82.5 |
| 20 months at 40° C | 82.1 |
| 25 months at 40° C | 71.3 |
| 57 weeks at RT | 91.6 |
| 25 months at 30° C | 82.5 |

Based on these data, it is estimated that the formula will be stable for at least 3 years at room temperature.

C. Formula for 50 mg/ml.

| | | |
|---|---|---|
| Ampicillin Trihydrate at 86% | 5.87 | Gm. |
| Sucrose, Powdered | 27.50 | Gm. |
| SYLOID (266-86) | 1.00 | Gm. |
| Propylparaben milled | 0.10 | Gm. |
| Tertiary butyl hydroquinone | 0.02 | Gm. |
| Citric Acid Anhydrous | 0.01 | Gm. |
| Imitation Chocolate | 0.20 | ml. |

| -continued | | |
|---|---|---|
| Cocoa | 1.00 | Gm. |
| Sesame Oil, q.s. | 100 | ml. |

Ampicillin permanent suspension as described in 2.C. (except that imitation orange wonf was substituted for the chocolate and cocoa) was compared with a Commercial Ampicillin Aqueous Suspension. (PENBRITIN, Ayerst, McKenna & Harrison, Ltd.). The equivalency between these two dosage forms in a crossover 18-subject bioavailability study was clearly demonstrated.

Stability Data (2.C.)

| Storage Conditions | Ampicillin Recovered |
|---|---|
| Initial | 47 mg/ml |
| 1 day at 74° C | 44.6 |
| 2 days at 74° C | 40.1 |
| 7 days at 74° C | 16.2 |
| 1 week at 62° C | 44.0 |

Based on these data, it is estimated that the formula will be stable for about 3 years at room temperature.

3. Aspirin Permanent Suspension

A. Formula for 60 mg/Gm.:

| Aspirin | 6.0 | Gm. |
|---|---|---|
| Sucrose, Powdered | 27.5 | Gm. |
| SYLOID (266-86) | 1.0 | Gm. |
| Sesame Oil, q.s. | 100.0 | Gm. |

Stability Data

| Storage Conditions | Aspirin Recovered |
|---|---|
| Initial | 62.4 mg/Gm. |
| 1 day at 80° C | 54.1 |
| 4 days at 80° C | 41.3 |
| 4 days at 74° C | 47.5 |
| 3 months at 62° C | 56.8 |

Based on these data, it is predicted that the formula will be stable for at least one year.

B. Formula for 60 mg/Gm.

| Aspirin | 6.0 | Gm. |
|---|---|---|
| Sucrose, Powdered | 27.5 | Gm. |
| SYLOID (266-86) | 1.0 | Gm. |
| Glyceryl Mono-oleate, q.s. | 100.0 | Gm. |

Stability Data

| Storage Conditions | Aspirin Recovered |
|---|---|
| Initial | 58.8 mg/Gm. |
| 1 day at 80° C | 47.6 |
| 4 days at 80° C | 38.2 |
| 4 days at 74° C | 44.9 |
| 3 months at 62° C | 54.8 |

Based on these data, it is estimated that the formula will be stable for at least one year at room temperature.

C. Formula for 60 mg/Gm.

| Aspirin | 6.00 | Gm. |
|---|---|---|
| Sucrose, Powdered | 27.50 | Gm. |
| SYLOID (266-86) | 1.00 | Gm. |
| Propylparaben | 0.10 | Gm. |
| Ter. Butylhydroquinone | 0.02 | Gm. |
| Citric Acid Anhydrous | 0.01 | Gm. |
| Imitation Banana | 0.35 | Gm. |
| Sesame Oil, q.s. | 100.00 | Gm. |

4. Amoxicillin Probenecid Suspension

| -continued | | |
|---|---|---|
| A. Formula for Amoxicillin 150 mg/ml and Probenecid 50 mg/ml: | | |
| Amoxicillin Trihydrate | 15.0 | Gm. |
| Probenecid | 5.0 | Gm. |
| Sucrose, Powdered | 20.00 | Gm. |
| SYLOID (266-90) | 0.5 | Gm. |
| Propylparaben | 0.1 | Gm. |
| Tertiary Butylhydroquinone | 0.02 | Gm. |
| Citric Acid | 0.01 | Gm. |
| Imitation Banana Flavor | 0.2 | ml. |
| Sesame Oil, q.s. | 100 | |

Stability Data

| Storage Conditions | Amoxicillin Recovered | Probenecid Recovered |
|---|---|---|
| Initial | 143.3 mg/ml | 51.1 mg/ml |
| 8 hrs. at 80° C | 137.2 | — |
| 16 hrs. at 80° C | 138.7 | — |
| 1 day at 80° C | 131.8 | 48.8 |
| 3 days at 80° C | 80.8 | — |
| 3 days at 74° C | 129.9 | 51.9 |
| 5 days at 74° C | 122.2 | 46.4 |
| 7 days at 74° C | 110.9 | 49.8 |
| 17 days at 62° C | 133.1 | — |
| 5 weeks at 62° C | 120.7 | 46.0 |
| 7 weeks at 62° C | 111.4 | 50.4 |
| 10 weeks at 62° C | 84.9 | 50.0 |
| 3 months at 51° C | 133.6 | 47.6 |

Based on these data, it is estimated that the formula will be stable for at least 3 years at room temperature.

| B. Formula for Amoxicillin 100 mg/ml and Probenecid 50 mg/ml: | | |
|---|---|---|
| Amoxicillin Trihydrate | 10.00 | Gm. |
| Probenecid | 5.00 | Gm. |
| Sucrose, Powdered | 25.00 | Gm. |
| SYLOID (266-90) | 0.50 | Gm. |
| Propylparaben | 0.10 | Gm. |
| Tertiary Butylhydroquinone | 0.02 | Gm. |
| Citric Acid | 0.01 | Gm. |
| Imitation Banana Flavor | 0.20 | ml. |
| Sesame Oil, q.s. | 100.00 | ml. |

| Storage Conditions | Amoxicillin Recovered | Probenecid Recovered |
|---|---|---|
| Initial | 109.2 mg/ml | 51.5 mg/ml |
| 8 hrs at 80° C | 104.6 | 49.8 |
| 16 hrs. at 80° C | 102.9 | 50.7 |
| 1 day at 80° C | 101.8 | 52.6 |
| 2 days at 80° C | 90 | 48.4 |
| 1 day at 74° C | 105.7 | 50.9 |
| 3 days at 74° C | 98.5 | 51.5 |
| 5 days at 74° C | 93.2 | 54.3 |
| 7 days at 74° C | 67.3 | 52.0 |
| 1 week at 62° C | 107.2 | 50.3 |
| 2 weeks at 62° C | 100.1 | 50.7 |
| 3 weeks at 62° C | 93.8 | 56.1 |
| 4 weeks at 62° C | 87.2 | 52.4 |
| 2 months at 51° C | 112.7 | 58.3 |

Based on these data, it is estimated that the formula will be stable for at lease 3 years at room temperature.

5. Amoxicillin Permanent Suspension

A. Formula for 50 mg/Gm.:

| Amoxicillin Trihydrate | 5.00 | |
|---|---|---|
| Saccharide* | 27.50 | Gm. |
| SYLOID (266-86) | 1.00 | Gm. |
| Tertiary Butyl Hydroquinone | 0.02 | Gm. |
| Propylparaben | 0.10 | Gm. |
| Citric Acid | 0.01 | Gm. |
| Imitation Chocolate | 0.20 | Gm. |
| Sesame Oil q.s. | 100.00 | Gm. |

*Saccharides chosen for stability evaluation were sorbitol, mannitol, lactose, glucose, fructose, or sucrose.

B. Stability Data

-continued

| Storage Conditions | Sorbitol | Mannitol | Lactose | Glucose | Fructose | Sucrose |
|---|---|---|---|---|---|---|
| Initial | 100 | 100 | 100 | 100 | 100 | 100 |
| 1 week at 80° | Nil | Nil | Nil | Nil | Nil | 69.2 |
| 2 weeks at 51° | 89.3 | 96.3 | 101.3 | 76.4 | 64.7 | — |
| 28 weeks at RT | 103.9 | 104.1 | — | 101.2 | 99.2 | 102.4 |

Based on the 1 week data, sucrose is the preferred saccharide for the Amoxicillin Permanent Suspension.

Although the silica agents described are highly preferred other thixotropic agents can be employed to thicken the vegetable oil vehicles of this invention. Exemplary are such agents selected from carbohydrates, proteins, cellulose derivatives, polysaccharides from plant and marine sources, synthetic polymers, silicates and other conventional thickners. Thickening of the vegetable oil vehicle can be achieved with effective amounts of calcium silicate, CARBOPOL 960 or 934 (an ammonium salt or free acid form, respectively, of an acrylic acid polymer with sucrose polyalkylether linkages, available from B. F. Goodrich Chemical Co.), Thixcin R and Thixcin E (Available from The Baker Castor Oil Co., Bayonne, N.J.). Generally the effective amounts employed fall below 5% of the total system on a weight basis.

In certain cases it may be desirable to prepare "sugar-free" permanent suspensions. Such suspensions can be prepared by employing an effective amount of a silica agent of the type above described in place of the sugar in any of the suspensions of this invention. Such formulations constitute another embodiment of this invention.

Precoating the drug component of the suspensions herein described with a natural or synthetic macromolecule, eg. any pharmaceutically acceptable macromolecule, or mixture therefo, compatible with said suspensions, constitutes another embodiment of this invention. Kitasamycin and Cloxacillin are examples of drugs which can be formulated using this technique.

We claim:

1. An anhydrous pharmaceutical vehicle suitable for oral administration of a water sensitive drug permanently suspended therein, wherein said water sensitive drug is a cephalosporin, said vehicle consisting essentially of:
   a. about 5 to about 60 percent by weight of a sugar suspending agent selected from the class consisting of sucrose, lactose, fructose, glucose, mannitol, and sorbitol;
   b. about 0.1 to about 5 percent by weight of a pharmaceutically acceptable silica thickening agent having a particle size of about 2 to about 4 microns, an alkaline pH (5 percent slurry in water) no higher than 8, and an oleophilicity of about 1;
   c. The remainder being a pharmaceutically acceptable vegetable oil comprising monoglyceride, diglyceride or triglyceride of a saturated fatty acid containing 14 to 22 carbon atoms or monoglyceride, diglyceride or triglyceride of an unsaturated fatty acid containing 14 to 22 carbon atoms.

2. The vehicle of claim 1 wherein the sugar suspending agent is sucrose.

3. The vehicle of claim 1 wherein the vegetable oil is sesame oil.

4. The vehicle of claim 1 wherein the sugar is present in amounts of about 20 to about 40 percent and the silica is present in amounts of about 0.5 percent to about 1.5 percent.

* * * * *